United States Patent
Yurchak

(10) Patent No.: US 7,232,936 B1
(45) Date of Patent: Jun. 19, 2007

(54) CONVERSION OF OXYGENATE TO OLEFINS WITH STAGED INJECTION OF OXYGENATE

(75) Inventor: Sergei Yurchak, Media, PA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 09/507,838

(22) Filed: Feb. 22, 2000

(51) Int. Cl.
*C07C 1/20* (2006.01)

(52) U.S. Cl. .................... 585/640; 585/639; 585/638

(58) Field of Classification Search ................ 585/639, 585/638
See application file for complete search history.

(56) References Cited

U.S. PATENT DOCUMENTS

| 3,751,504 A | 8/1973 | Keown et al. ............. 585/323 |
| 3,911,041 A | 10/1975 | Kaeding et al. ............. 260/682 |
| 4,377,713 A | 3/1983 | Sato et al. ................. 585/467 |
| 4,377,718 A | 3/1983 | Sato et al. |
| 4,761,513 A | 8/1988 | Steacy ...................... 585/467 |
| 5,120,890 A | 6/1992 | Sachtler et al. ............. 585/449 |
| 5,925,586 A | 7/1999 | Sun ............................ 502/62 |
| 6,642,426 B1 | 11/2003 | Johnson et al. |

FOREIGN PATENT DOCUMENTS

| WO | 96/15082 | 5/1996 |
| WO | WO 99/15482 | * 4/1999 |
| WO | WO 01/62689 | 8/2001 |

OTHER PUBLICATIONS

Keim, K. H., et al. *"The Methanol-to-Gasoline (MTG) Process: Status Report on 100 BPD Fluid Bed Pilot Plant"*, C-16, pp. 2-160 through 2-166.

* cited by examiner

*Primary Examiner*—Thuan Dinh Dang

(57) ABSTRACT

A system and process for producing olefins from oxygenate, e.g., methanol or dimethylether, includes a fluidized bed reaction zone that provide contact between the oxygenate and a molecular sieve catalyst such as ZSM-34 or SAPO-34. Improved ethylene selectivity is realized when the oxygenate is stagewise injected into the fluidized bed at one or more locations along the axial direction of the fluidized bed reaction zone.

16 Claims, 1 Drawing Sheet

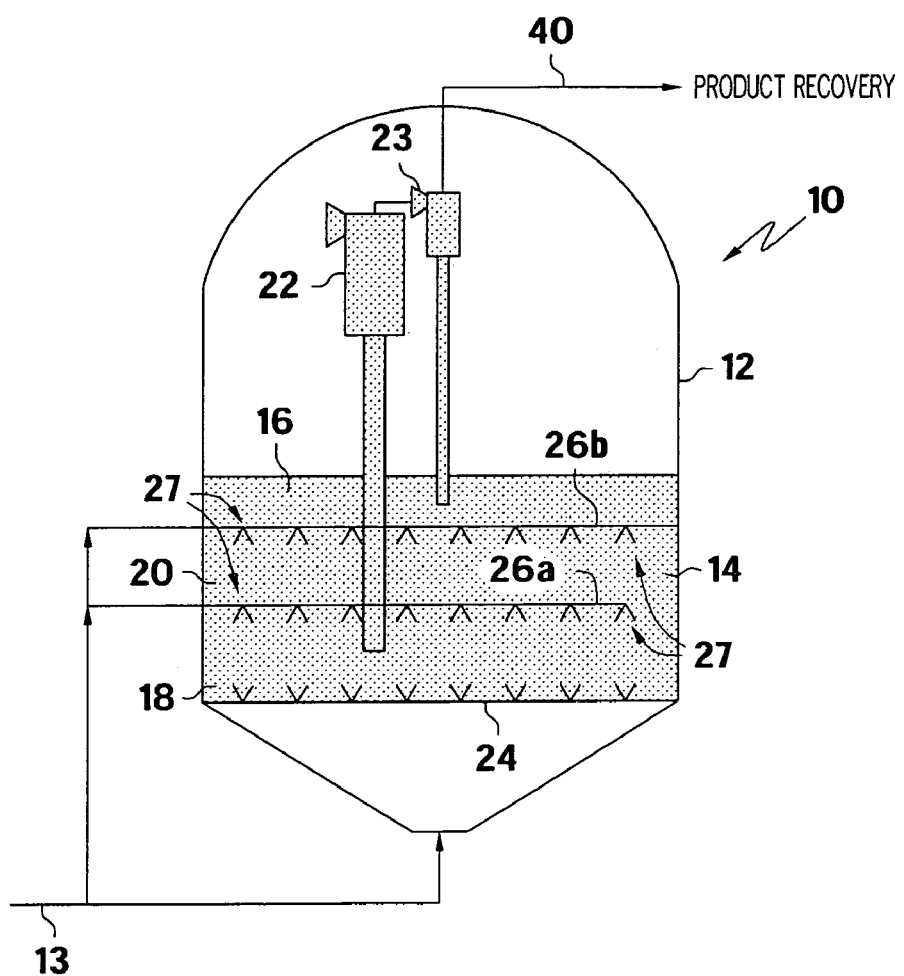
Figure

CONVERSION OF OXYGENATE TO OLEFINS WITH STAGED INJECTION OF OXYGENATE

BACKGROUND OF THE INVENTION

A. Field of the Invention

The present invention relates to a process for converting oxygenate, such as methanol and/or dimethylether, to olefins in a reactor over a molecular sieve catalyst such as ZSM-34 and SAPO-34 wherein oxygenate is introduced to a catalyst bed at multiple injection points along the flow axis of the reactor. The process is especially useful for increasing ethylene selectivity.

B. Description of the Prior Art

Olefin manufacturing processes, such as steam cracking, generally operate at low pressure, high temperature, and with diluents, such as steam, to enhance yields of light olefins which are thermodynamically favored by these conditions. In producing light olefins, the selectivity to ethylene can be increased to some extent by increasing reactor severity, e.g. by operation at low pressure, high temperature, and/or by diluent addition. However, as reactor severity is increased total olefin production is decreased. Moreover, the production of paraffins, i.e., methane, ethane, propane, etc., aromatics and other less desirable components will also increase. Similarly, diluent addition entails significant expense. For example, with steam diluent, the expense of generating the steam and the costly equipment to condense the steam for product recovery must be considered with the additional revenues attained for the higher olefin yields. Furthermore, all equipment must be increased in size to handle the processing of diluent as well as reactive feed. With methanol conversion processes, these expenses generally negate using diluents in significant quantity.

In an effort to improve yields in various reaction procedures, stagewise injection of reagents has been used in various fixed bed processes. For example, U.S. Pat. Nos. 4,377,718 and 4,761,513 describe toluene alkylation processes wherein the alkylating reagent is fed at different stages between fixed beds. Likewise, U.S. Pat. No. 3,751,504 discloses a similar procedure, using multiple injection ports, for preparing ethylbenzene using a fixed bed catalyst reactor. U.S. Pat. No. 5,120,890 discloses multiple reactant injection locations into separate fixed beds in a process for reducing benzene and toluene content in light gasoline streams. U.S. Pat. Nos. 3,751,504; 4,377,718; 4,761,513; and 5,120,890 are each entirely incorporated herein by reference. In these fixed bed processes, one can easily separate the catalyst load into several different and discrete zones. During use, product from one zone is mixed with additional methanol, and this mixture is fed to the subsequent zone. One way of providing these separate and discrete zones includes placing each zone in a separate reactor vessel, wherein additional reagent(s) is (are) injected between adjacent zones. This procedure suffers from the drawback that considerable expense is involved in providing separate reactor vessels and the associated hardware for running this type of system. Additionally, fixed bed reactors are disadvantageous for exothermic reactions because of the potential negative impact of exotherms on product selectivity. Reactor stability concerns with fixed beds also require that the temperature rise per catalyst bed be limited. This could necessitate a large number of beds to accommodate the heat of reaction.

U.S. patent application Ser. No. 09/166,188, filed Oct. 5, 1998 describes multiple methanol injection into a fluid bed to increase p-xylene selectivity and methanol utilization.

SUMMARY OF THE INVENTION

It is an object of this invention to provide processes and systems for converting oxygenate to olefins, especially lower olefins, e.g., ethylene, propylene and butene, with high conversion and selectivity. It has now been found that by using multiple injection of pure or slightly diluted feed into, e.g., a fluid-bed reactor system, it is possible to achieve ethylene selectivity improvements comparable to those achieved with large amounts of diluents, at less expense.

In general, the processes and systems according to this invention use stagewise injection of oxygenate by introducing the oxygenate into a catalyst bed at plural stages along the flow axis of the reactor.

In one aspect, the present invention relates to a process for converting oxygenate to an olefin-containing product, comprising:

introducing oxygenate into a reactor system at plural stages along a flow axis of a reactor catalyst bed;

contacting the oxygenate with an oxygenate to olefin conversion molecular sieve catalyst under oxygenate to olefin conversion conditions; and recovering an olefin-containing product which contains a higher proportion of ethylene than a product produced from a process which differs only by introducing oxygenate at a single stage along the flow axis of the reactor catalyst bed.

In another embodiment, the present invention relates to a system for converting oxygenate to an olefin-containing product, comprising:

a reactor system comprising a reactor catalyst bed;

means for introducing oxygenate into the reactor system at plural stages along a flow axis of said reactor catalyst bed;

means for contacting the oxygenate with an oxygenate to olefin conversion molecular sieve catalyst under oxygenate to olefin conversion conditions; and means for recovering an olefin-containing product which contains a higher proportion of ethylene than a product produced from a process which differs only by introducing oxygenate at a single stage along the flow axis of the reactor catalyst bed.

BRIEF DESCRIPTION OF THE DRAWING

This invention, and the advantageous features thereof, will be more completely understood when considered in context with the following detailed description, which includes a description of the attached drawing, wherein:

The FIGURE illustrates an embodiment of the invention that uses a single reactor vessel that includes a single fluidized bed and a multiple injection arrangement.

DETAILED DESCRIPTION OF THE INVENTION

It is known to selectively convert oxygenates, including particularly methanol, to light olefins, viz., ethylene ($C_2^=$), propylene ($C_3^=$), and butylene ($C_4^=$). Ethylene and propylene are in high demand, and the need for these chemical raw materials, particularly ethylene, continues to grow. In the present invention, oxygenate, e.g., oxygenate selected from the group consisting of methanol and dimethylether, is reacted at elevated temperature over a bed of a molecular sieve catalyst, e.g., ZSM-5, ZSM-34 or SAPO-34, to produce a reaction product from which $C_2$–$C_4$ olefins are recovered.

The conversion of oxygenate to olefin according to the present invention may occur in a reactor of any configuration. Continuous reactors, such as dense fluidized bed, riser, fast fluid-bed, or fixed bed, are suitable configurations for use in the present invention. Preferably, the reactor is a fluidized bed flow reactor type. The catalyst may be used in various forms, such as a fixed bed, moving bed, fluidized bed, e.g., a dense fluid bed, in suspension in the generally gaseous reaction mixture.

In one aspect of the invention, the reactor catalyst bed comprises a fluidized bed reaction zone which includes a top portion, a bottom portion, and an intermediate portion extending between the top portion and the bottom portion. Oxygenate is introduced at a first location at or near the bottom portion of the fluidized bed reaction zone, and at a second location in the intermediate portion of the fluidized bed reaction zone. Oxygenate can be introduced to the fluidized bed reaction zone at a plurality of different axial positions in the intermediate portion of the fluidized bed reaction zone.

Oxygenate can be introduced directly into the bottom portion of the reaction zone through a bottom grid, and in the intermediate or top portion of the reaction zone through injectors. The bottom grid can comprise downstream or upstream directed nozzles; intermediate or top portion injectors are preferably directed upstream, but may be directed downstream as well. This aspect of the invention is not critical, as several different injector designs are feasible and the actual layout depends on the specifics of the design. For example, with a pipe grid layout for the bottom grid, the injectors can be facing upstream and even be angled relative to the vertical axis.

Oxygenate can be introduced at a plurality of different locations within a plane perpendicular or substantially perpendicular to the axial direction of the reactor vessel, i.e., a single plane may comprise a plurality of means for introducing oxygenate, arranged in any suitable configuration such as a straight line, ring, and/or grid of oxygenate feed outlets, e.g., nozzles. Due to spatial constraints, it may be necessary to locate the nozzles at slightly different elevations within a set of injectors.

Minor amounts, say, 0.01–10 wt. %, of aromatics such as benzene, toluene, and/or xylenes, etc. can be co-fed with the oxygenate in order to enhance olefin selectivity.

The FIGURE schematically illustrates a fluidized bed reactor system that can be used in this invention for converting oxygenate to olefin-containing product. The illustrated system is described in detail below.

The FIGURE illustrates a relatively compact and simple embodiment of the system 10 according to the invention. The system 10 includes a reactor vessel 12, which contains a single fluidized bed reaction zone 14. This reaction zone 14 includes a top portion 16, a bottom portion 18, and an intermediate portion 20 that extends between the top portion 16 and the bottom portion 18.

A fluidized bed reaction zone 14, as is known in the art, contains a volume of small sized particles that are generally kept afloat ("fluidized") by flowing gas as it passes upward through the reactor vessel 12 during reactor operation. Conventional devices, such as primary cyclone 22 and secondary cyclone 23, can be used to provide separation and recovery of entrained catalyst from the gas, to return the solids to the bed, and to maintain the fluidized bed 14 under suitable operating conditions. Through this gas flow, reactants pass into and/or through the reaction zone 14, and the small particles provide a large surface area that allows generous contact between the reactants and catalyst under the oxygenate conversion conditions.

Preferably, the fluidized bed 14 will contain a catalyst that promotes the oxygenate conversion reaction, and indeed, if desired, the entire volume of the fluidized bed 14 may comprise catalyst particles. Any suitable catalyst can be used without departing from the invention.

The catalyst employed in the present invention may comprise a shape-selective zeolite having a Constraint Index of 1–12. Details of the Constraint Index test procedures are provided in J. Catalysis 67, 218–222 (1981) and in U.S. Pat. No. 4,711,710 Chen et al, which are incorporated by reference. Preferred shape selective zeolites are exemplified by ZSM-5, ZSM-11, ZSM-12, ZSM-23, ZSM-35, ZSM-38, ZSM-48, ZSM-57 and similar materials. ZSM-5 is described in U.S. Pat. No. 3,702,886, U.S. Reissue 29,948 and in U.S. Pat. No. 4,061,724 (describing a high silica ZSM-5 as "silicalite"). ZSM-11 is described in U.S. Pat. No. 3,709,979. ZSM-12 is described in U.S. Pat. No. 3,832,449. ZSM-23 is described in U.S. Pat. No. 4,076,842. ZSM-35 is described in U.S. Pat. No. 4,016,245. ZSM-38 is described in U.S. Pat. No. 4,046,859. ZSM-48 is described in U.S. Pat. No. 4,397,827. ZSM-57 is described in U.S. Pat. No. 4,873,067. These patents are incorporated by reference.

Other suitable catalysts for use in the present invention include molecular sieves of pore size ranging from about 5.0 Angstroms to about 4.0 Angstroms, preferably from about 4.8 Angstroms to about 4.4 Angstroms. The small pore molecular sieve employed in the reaction is of pore size ranging between about 5.0 Angstroms and 4.0 Angstroms, preferably about 4.8 Angstroms and 4.4 Angstroms, and comprised of a crystalline framework oxide component. Generally, the pore apertures of the molecular sieve structure consist of from about 6- to about 10-, preferably 8-membered ring structures. These materials, employed in accordance with this invention, include natural and synthetic crystalline structures with tetrahedral framework oxide components such as aluminum, silicon, phosphorus and the like. Such catalysts are preferably selected from the group consisting of zeolites, tetrahedral aluminophosphates (ALPOs) and tetrahedral silicoaluminophosphates (SAPOs). Exemplary of small pore zeolitic catalysts are ZSM-34 described in U.S. Pat. No. 4,086,186, incorporated herein by reference, ZK4, ZK-5, zeolite A, zeolite T, chabazite, gmelinite, clinoptilolite, erionite, ZSM-35, rho, offretite and the like; and such non-zeolitic catalysts as levyne, SAPO-17, SAPO-18, SAPO-34, SAPO-43 and SAPO-44. The SAPOs are variously described in U.S. Pat. Nos. 4,440,871; 4,554,143; 4,567,029; 4,666,875; and 4,742,033, incorporated herein by reference.

The present invention may also be used with methods which modify the framework structure of the catalyst to increase light olefin production, especially the $C_2^=/C_3^=$ ratio, while producing as little of the paraffinic and aromatic by-products as possible. For example, U.S. Pat. No. 3,911,041, discloses a process for converting oxygenate to a reaction product containing light olefins by contact of the oxygenate with a phosphorus modified zeolite. A zeolite of intermediate pore size, such as ZSM-5, is modified by incorporating from about 0.78 wt. % to 4.5 wt. % phosphorus bonded to its structural framework. Typically the dry ZSM-5 zeolite is contacted with a solution of a phosphorus-containing compound, e.g., $PCl_3$, and heated at elevated temperature for a time sufficient to incorporate the phosphorus within the crystalline framework of the zeolite.

Selectivated catalysts (i.e., catalysts treated to preferentially produce a particular compound) can be used in the process of the invention. Such selectivated catalysts are known in this art. Selectivated small pore zeolitic catalysts of the type described above, e.g., ZSM-34 are particularly useful. Selectivation of such materials can be carried out by conventional methods such as phosphorus modification. Examples of selectivated small pore materials suitable for use in the present invention can be found in U.S. Pat. No. 5,925,586 to Sun, incorporated herein by reference, which discloses treatment of molecular sieve with phosphonitrilic oligomers.

For the reaction to proceed, the oxygenate-containing feed with or without optional diluent, e.g., steam, water, hydrogen, nitrogen, and/or light hydrocarbon gas, can be introduced via feed line 13 into the fluidized bed reaction zone 14 at plural locations. In the illustrated embodiment the oxygenate is introduced at plural locations in the fluidized bed reaction zone 14; preferably these locations include one at or near its bottom portion 18. The oxygenate reactant preferably is introduced in gaseous form and provides at least a portion of the gas flow necessary for maintaining the reaction zone 14 in fluidized form. This reactant can be introduced using any appropriate introduction device 24, including conventional devices known in the art (e.g., injector nozzles, perforated grids, pipe grids, etc.).

The illustrated reactor system includes two downstream axial introduction devices 26a and 26b in addition to the introduction device 24 located upstream at the bottom portion 18 of the fluidized bed reaction zone for introducing oxygenate in additional "stages." These devices 26a and 26b may be arranged to introduce the oxygenate reagent in any appropriate manner. For example, each device 26a and 26b may include one, and preferably more, injector nozzles 27 located around the periphery of the reactor vessel 12 for introducing the oxygenate reagent around the vessel periphery. As another alternative, each device 26a and 26b may include a manifold or pipe grid arrangement for introducing the oxygenate reagent at a plurality of locations in the interior of the fluidized bed reaction zone 14. Preferably, each axial stage includes suitable devices for introducing the reactant at plural locations within the stage itself. This stagewise introduction of oxygenate at various multiple locations increases selectivity to lower olefins, e.g., ethylene. Because staging the feed in the manner described reduces the effective contact time, conversion will decrease. Conversion can be maintained by increasing catalyst activity, e.g., by increasing the concentration of active component in the catalyst. Other ways are feasible, depending on the particular catalyst. Alternatively, the conversion can be allowed to decrease; this will usually result in further increases in light olefin selectivity, as olefin selectivity decreases somewhat with increases in conversion.

Also, if desired, another oxygenate reagent introduction device or port can be provided at or around the top portion 16 of the fluidized bed, without departing from the invention.

Oxygenate and optional diluent can be mixed together prior to introducing the materials into the bottom 18 of the fluidized bed reaction zone 14, such that these materials are introduced in a common feed stream. Alternatively, the materials can be introduced separately into the fluidized bed reaction zone 14 and contacted together after their introduction, or the materials can be first mixed together in a nozzle or other device that introduces both concurrently into the fluidized bed reaction zone 14. Any suitable mixing device and method can be used for this introduction without departing from the invention.

If necessary, the devices 24 and 26 for introducing the oxygenate and optional diluent can be maintained under conditions ensuring the integrity of these materials until the reactants or reagents enter the catalyst bed (i.e., to prevent undesired side reactions, conversions, and/or degradation of the reactants or reagents). This can be accomplished in any suitable manner, such as by limiting residence time of the materials in the introduction device or by cooling the introduction device to a temperature that maintains the reagent or reactant under stable conditions or by lining the injector assembly either internally or externally with refractory or inert type material. Inasmuch as oxygenate conversion is exothermic, heat can be removed from the reaction zone by any suitable means, e.g., by immersing heat exchange surfaces with the fluidized bed and generating steam (not shown). Some of the exothermic heat could also be removed by injecting some of the reactant and/or diluent as liquid either in the lower zone or in the injector zones. Because diluent effects are generally believed to arise from partial pressure effects, multiple injection might enhance ethylene selectivity by allowing operation at lower oxygenate partial pressures.

The reactor vessel 12 and the reactant introduction rates are maintained under suitable conditions to support a catalytic oxygenate conversion to olefin-containing product reaction to produce the desired product. This reaction product preferably is produced in a gaseous form, and it may be collected and recovered from the reactor outlet stream 40 in any suitable manner, such as by condensation, compression, and subsequent fractionation of the hydrocarbon liquid using conventional distillation and recovery equipment. Further purification of the product can be accomplished in any suitable manner, for example, by selective hydrogenation.

Unreacted feeds can be recycled to the fluidized bed reaction zone 14. It is generally not necessary to completely purify the recycled oxygenate, although this can be done, if desired. Any dimethylether product formed can also be recycled back to the reactor for conversion to olefinic products.

In accordance with the present invention, an oxygenated feed, e.g., methanol, suitably with added optional diluent, is contacted with a fixed, moving, or fluidized bed, or beds, of the above catalyst at reaction conditions, typically and preferably within the ranges given below:

| Major Operating Variable | Typical Range | Preferred Range |
|---|---|---|
| Temperature, °C. | 250 to 650 | 350 to 600 |
| Pressure, kPa | 100 to 1500 | 170 to 1150 |
| Flow Rate, WHSV ($hr^{-1}$) | 0.01 to 5000 | 0.5 to 2000 | to obtain an effluent from which the ethylene, and other products, is recovered.

The process can be conducted in the presence of added diluent, e.g., hydrogen and/or added water such that the molar ratio of diluent to oxygenate in the feed to the reactor is between about 0.01 and about 10. Those skilled in the art will be capable of adjusting the various reaction parameters and conditions to optimize conversion, yield, and selectivity, using routine experimentation.

This invention relates to novel reactor systems and processes for improving lower olefin, e.g., ethylene, selectivity in a fluidized bed reactor. The systems and processes according to the invention provide these improved results by introducing the oxygenate into an upstream location of the reactor system as well as at one or more locations downstream in the reactor system, i.e., in a "stagewise manner." Any number of downstream "stages" can be used for introducing the oxygenate reagent, e.g., two to four downstream stages. Placing more than four injectors within the reactor is technically feasible, but there will be practical limits due to, e.g., maintenance considerations. In addition, there will be a point of diminishing returns. As the number of injectors increases, the incremental improvement in yields decreases.

The fluidized beds used in the present invention can be relatively dense, such as turbulent sub-transport fluid beds with an operating bed density of about 200 to 700 kg/m$^3$, preferably about 300 to 500 kg/m$^3$. The use of these dense beds increases the catalyst concentration at the area of oxygenate injection.

A suitable alternate fluid bed design is termed a fast fluid bed. This is typically characterized by a bed density that is lower than that prevailing in a dense fluid bed. Superficial gas velocities are typically greater than 5 feet/second. The fluidized bed in a fast fluid bed is less defined than that in a dense fluid bed.

Another suitable reactor system is a riser "fluid bed" reactor. In this case the classical fluidized bed does not exist but rather solid catalyst particles and gas are flowed up or down the reactor vessel in a more or less homogeneous manner. Typically solids density in the riser is less than about 100 kg/m$^3$, and the superficial gas velocity is in excess of 20–40 feet/second.

Liquids can be injected into all three types of fluid bed systems mentioned above.

The catalyst inventory of the fluidized beds can be maintained by return of solids to the beds from the cyclone recovery system, but small losses will occur, e.g., due to attrition. Losses can be made up by adding catalyst to maintain catalyst inventory.

The olefin-containing product in the system according to the FIGURE is collected from the hydrocarbon liquid and can be further processed, e.g., by condensation, compression and fractionation, as described above.

The following examples are provided to more fully illustrate the invention and accent its advantageous features. These examples are included to illustrate the invention and should not be construed as limiting it in any way.

EXAMPLE 1

Catalytic tests were carried out with 15 g catalyst in a small fluid-bed reactor at atmospheric pressure, 375–470° C. and methanol WHSVs of 0.15–0.7 g methanol/g cat-hr. Water was used as the diluent. Pure methanol feed was used except when diluent was present. Two catalysts were tested: ZSM-34 and SAPO-34. The ZSM-34 catalyst was bound with a silica binder and steamed for 6 hrs at 538° C. with 1 atm steam. The SAPO-34 catalyst was bound in a silica-alumina matrix and steamed for 8 hrs at 538° C. with 1 atm steam. Test results are summarized in Table 1.

As shown, both catalysts were very efficient in converting methanol to a hydrocarbon product rich in light olefins. Also, water diluent had a beneficial effect on improving the conversion of methanol to ethylene. The effect of diluent appears more pronounced with the SAPO-34 catalyst.

TABLE 1

Catalytic Test Data: Methanol to Light Olefins

| Water Diluent, wt. % of Feed | Catalyst | | | |
|---|---|---|---|---|
| Yields, Wt. % | ZSM-34 | | SAPO-34 | |
| of Methanol | 0 | 70 | 0 | 70 |
| Methanol | 4.3 | 4.0 | 0.1 | 0.1 |
| Ethylene | 22.8 | 25.3 | 19.8 | 26.4 |
| Propylene | 13.0 | 9.7 | 15.7 | 12.4 |
| Butenes | 2.5 | 1.9 | 4.1 | 2.2 |
| Other HC | 3.6 | 5.1 | 4.2 | 2.8 |
| Water | 53.8 | 54.0 | 56.2 | 56.2 |
| Total | 100.0 | 100.0 | 100.0 | 100.0 |

The benefit of multiple injection was estimated from the data in Table 1 for a schematic of the multiple injection arrangement shown in the FIGURE. ZSM-34 data indicate that multiple injection can significantly improve ethylene selectivity, as shown in Table 2. Pure methanol is introduced in all feed injections.

TABLE 2

Benefit for Multiple Injection with ZSM-34

| Number of Injectors | 0 | 1 | 2 | 3 |
|---|---|---|---|---|
| $C_2^=$ Selec., wt. % of Methanol Conv. | 22.8 | 23.6 | 24.1 | 24.4 |
| Methanol Conversion, wt. % | 95.7 | 89 | 86 | 84 |

The case with no injector has the feed entering through the bottom grid in the reactor. With three intermediate injectors, the ethylene selectivity is almost what it would be with 70 wt. % water diluent. The estimated benefit shown in Table 2 does not include that expected from the decreased conversion level. Conversion could be increased by increasing catalyst activity.

Similarly, multiple feed injection is beneficial with SAPO-34 catalyst, as shown in Table 3.

TABLE 3

Benefit for Multiple Injection with SAPO-34

| Number of Injectors | 0 | 1 | 2 | 3 |
|---|---|---|---|---|
| $C_2^=$ Selec., wt. % of Methanol Conv. | 19.8 | 22.1 | 23.4 | 24.1 |
| Methanol Conversion, wt. % | 99.9+ | 99 | 98 | 96 |

Ethylene selectivity improvements from using 4 feed injection zones are 7% and 22%, respectively, for ZSM-34 and SAPO-34 catalysts. Enhanced ethylene selectivity is thus achieved without resorting to diluents, which entail significant operating and capital costs. Again, the estimated benefit shown in Table 3 does not include that expected from the decreased conversion level. Conversion could be increased by increasing catalyst activity.

EXAMPLE 2

In a toluene alkylation process, a feed of 1.8–2.0 toluene to methanol molar ratio was reacted over a phosphorus-modified ZSM-5 at 0.25 overall methanol WHSV to produce p-xylene. Multiple injection of methanol is used to improve p-xylene yield and methanol utilization. Some of the methanol reacts to form olefins. The pertinent data were examined to determine if there was improvement in ethylene selectivity with the number of methanol injectors. The results in Table 4 indicate a positive effect of multiple injection on ethylene selectivity in this process. Again, no injectors means the feed enters the reactor through the bottom grid. The results are consistent with ethylene selectivity improvements with feed dilution in methanol conversion to light olefins over ZSM-5 catalyst. The catalyst activity referred to in Table 4 is for the reaction of toluene with methanol.

TABLE 4

Ethylene Selectivity in Toluene Alkylation Over ZSM-5

| | | | | |
|---|---|---|---|---|
| Rel. Apparent Catalyst Activity | 1 | | 2.8 | |
| No. of Methanol Injectors | 0 | 1 | 1 | 3 |
| $C_2^=$ in $C_1$–$C_4$ Hydrocarbon, wt. % | 46 | 48 | 50 | 51 |

While the invention has been described herein in terms of various preferred embodiments, those skilled in the art will recognize that various changes and modifications can be made without departing from the spirit and scope of the invention, as defined in the following claims.

What is claimed is:

1. A process for converting oxygenate to an olefin-containing product, comprising:
   introducing oxygenate into a reactor system at plural stages along a flow axis of a reactor catalyst bed;
   contacting said oxygenate with an oxygenate to olefin conversion molecular sieve catalyst under oxygenate to olefin conversion conditions; and
   recovering an olefin-containing product which contains a higher proportion of ethylene than a product produced from a process which differs only by introducing oxygenate at a single stage along a flow axis of the reactor catalyst bed wherein said oxygenate is selected the group consisting of methanol, dimethyl ether, and the mixture thereof, said reactor catalyst bed comprises a fluidized bed reaction zone which includes a top portion, a bottom portion, and an intermediate portion extending between the top portion and the bottom portion, wherein said oxygenate is introduced at a first location at or near the bottom portion of the fluidized bed reaction zone, and at a second location in the intermediate portion of the fluidized bed reaction zone.

2. A process according to claim 1, wherein the oxygenate is introduced into the intermediate portion of the fluidized bed reaction zone at plural locations provided at a plurality of different axial positions in the intermediate portion of the fluidized bed reaction zone.

3. A process according to claim 1, wherein the fluidized bed reaction zone is a dense fluid bed, and the oxygenate is introduced into the intermediate portion of the fluidized bed reaction zone at plural locations provided at a plurality of different axial positions in the intermediate portion of the fluidized bed reaction zone.

4. A process according to claim 1 wherein said catalyst comprises a molecular sieve selected from the group consisting of ZK-4, ZK-5, zeolite A, zeolite T, chabazite, gmelinite, clinoptilolite, erionite, ZSM-5, ZSM-11, ZSM-12, ZSM-23, ZSM-34, ZSM-35, ZSM-38, ZSM-48, ZSM-50, rho, offretite, ferrierite, levyne, SAPO-17, SAPO-18, SAPO-34, SAPO-43 and SAPO-44.

5. The process according to claim 4 wherein said catalyst comprises a phosphorus-modified molecular sieve.

6. The process according to claim 1 wherein said catalyst comprises a molecular sieve selected from the group consisting of ZSM-34 and SAPO-34.

7. The process according to claim 1 wherein said oxygenate is introduced to said process with a diluent.

8. The process according to claim 1 wherein said oxygenate is introduced to said process with minor amounts of an aromatic co-feed.

9. The process according to claim 1 wherein said reactor system is selected from the group consisting of dense fluidized bed, fast fluidized bed, riser or transport fluid bed, and fixed bed reactors.

10. The process according to claim 1 wherein said reactor system comprises a fluidized bed flow reactor.

11. The process according to claim 1 wherein said oxygenate is introduced directly into the bottom portion of the reaction zone through a bottom grid, and in the intermediate portion of the reaction zone through injectors.

12. The process according to claim 11 wherein the oxygenate is introduced at a plurality of different locations in a plane perpendicular or substantially perpendicular to the axial direction of the reactor vessel.

13. The process according to claim 11 wherein said bottom grid comprises downstream directed nozzles.

14. The process according to claim 11 wherein said bottom grid comprises upstream directed nozzles.

15. The process according to claim 11 wherein said intermediate portion injectors are directed upstream.

16. The process according to claim 11 wherein said intermediate portion injectors are directed downstream.

* * * * *